United States Patent [19]

Chu

[11] Patent Number: 4,922,055

[45] Date of Patent: May 1, 1990

[54] TOLUENE DISPROPORTIONATION CATALYZED BY A ZEOLITE CONTAINING FRAMEWORK GALLIUM

[75] Inventor: Cynthia T-W. Chu, Princeton Junction, N.J.

[73] Assignee: Mobil Oil Corporation, New York, N.Y.

[21] Appl. No.: 279,614

[22] Filed: Dec. 5, 1988

[51] Int. Cl.$^5$ ............................................. C07C 6/12
[52] U.S. Cl. ................................................... 585/470
[58] Field of Search ............................. 585/470, 475

[56] References Cited

U.S. PATENT DOCUMENTS

| | | | |
|---|---|---|---|
| 3,702,886 | 11/1972 | Argauer et al. | 423/328 |
| 4,160,788 | 7/1979 | Young | 585/475 |
| 4,180,689 | 12/1979 | Davies et al. | 585/407 |
| 4,182,923 | 1/1980 | Chu | 585/475 |
| 4,456,780 | 6/1984 | Young | 585/475 |

OTHER PUBLICATIONS

Oil and Gas Journal, vol. 69, No. 48 (1971), by Grandio et al., "AP-Catalyst Processes Make-Aromatics at Low Temperatures".

*Primary Examiner*—Patrick P. Garvin
*Assistant Examiner*—George R. Fourson
*Attorney, Agent, or Firm*—Alexander J. McKillop; Charles J. Speciale; Marina V. Schneller

[57] ABSTRACT

Disproportionation of toluene with high conversion thereof to produce benzene and xylenes is accomplished by subjecting toluene to disproportionation conditions in the presence of a catalyst comprising a crystalline silicate or crystalline aluminosilicate zeolite containing framework gallium, said zeolite having a silica to alumina ratio of at least about 12 and a constraint index, as hereinafter defined, within the approximate range of 1 to 12.

5 Claims, 1 Drawing Sheet

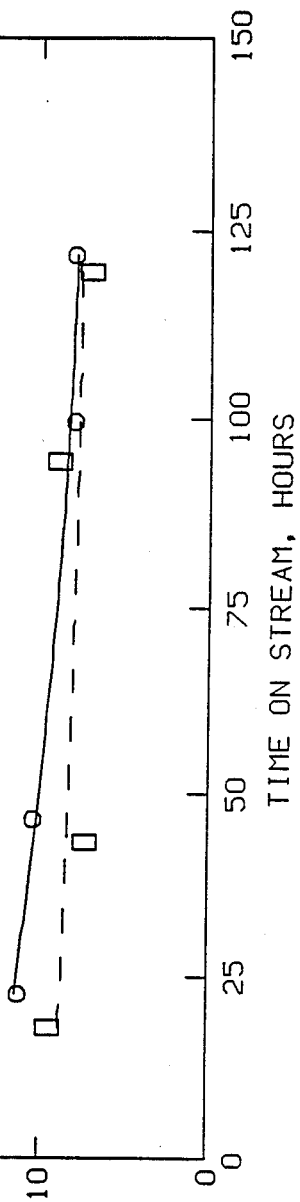

TOLUENE DISPROPORTIONATION CATALYZED BY A ZEOLITE CONTAINING FRAMEWORK GALLIUM

FIELD OF THE INVENTION

This invention relates to a catalytic process in which the catalyst affords high activity for disproportionation of toluene. The catalyst is a crystalline silicate or crystalline aluminosilicate zeolite catalyst containing framework gallium.

BACKGROUND OF THE INVENTION

The disproportionation of aromatic hydrocarbons in the presence of zeolite catalyst was reported by Grandio et al in the OIL AND GAS JOURNAL, Vol. 69, No. 48 (1971). Specific catalytic processes for disproportionation of toluene have been described in, for example, U.S. Pat. Nos. 4,160,788; 4,182,923 and 4,456,780.

Toluene disproportionation involves the conversion of toluene to benzene and xylene isomers, including ortho-, meta-and para-xylene. Meta-xylene is the least desired product, whereas, ortho- and para-xylene are the most desired isomers. Para-xylene, in substantial yield, is of particular value in the manufacture of terephthalic acid which is an intermediate in the manufacture of synthetic fibers such as "DACRON".

SUMMARY OF THE INVENTION

The present invention relates to a catalytic process for disproportionating toluene with high conversion thereof to yield benzene and xylenes, by subjecting toluene to disproportionation conditions defined below, in the presence of a catalyst comprising a crystalline silicate or crystalline aluminosilicate zeolite, which contains framework gallium, the zeolite having a silica to alumina ratio of at least about 12, a constraint index within the approximate range of 1 to 12.

The present process comprises disproportionation of toluene in the presence of the specified catalyst at a temperature between about 800° to 1100° F., and preferably at a temperature ranging from 850° to 950° F. The pressures of the catalytic disproportionation conditions range from about 100 to 800 psig.

DESCRIPTION OF THE DRAWING

FIG. 1 of the drawing is a graph in which percent toluene conversion of three catalysts is plotted against time on stream in hours.

DETAILED DESCRIPTION OF THE INVENTION

Zeolite catalysts have become widely used in processing petroleum in a production of various petrochemicals. Acid catalyzed reactions including disproportionation may be performed with the aid of these catalysts. Both naturally occurring and synthetically produced zeolites are known to catalyze certain acid catalyzed reactions. The naturally occurring zeolites were characterized by low silica:alumina ratios, that is they were aluminosilicates containing high amounts of framework aluminum. Research has been conducted to synthesize new zeolite structures having low framework aluminum atom content. One of the results of that research was the production of ZSM-5 zeolite characterized by great versatility. ZSM-5 is identified by an X-ray diffraction pattern, which is disclosed in U.S. Pat. No. 3,702,886, the disclosure of which is incorporated by reference herein.

The invention resides in the use of a particular ZSM-5 species containing predominantly framework gallium in the catalytic disproportionation of toluene. Disproportionation of toluene results in benzene and xylenes, including the xylene isomers ortho-xylene, meta-xylene and para-xylene. Disproportionation conditions of the process of the invention include temperatures ranging from 750° to 1100° F. and preferably from 850°–950° C. In the disproportionation process of the invention, the pressure ranges from 100 to 800 psig. The mole ratio of the hydrogen cofeed with the toluene containing feed can range from 0.1 to 20.

The framework gallium content of the ZSM-5 catalyst used in accordance with the invention can be expressed, in terms of weight percent Ga, as ranging from 0.1 to 15 percent, and preferably from 0.1 to 10 percent. Although the gallosilicate or galloaluminosilicate ZSM-5 can contain extra-zeolitic gallium, it is critical that the ZSM-5 species contain the framework gallium. That is, although the invention is directed to employing ZSM-5 containing framework gallium in toluene disproportionation, the zeolite species may also contain gallium exchanged, deposited, or physically admixed therein.

The framework gallium content of the ZSM-5 is critical, in the sense, that zeolites containing non-framework gallium, in the same amounts as the ZSM-5 species containing framework gallium will not produce the same degree of conversion as those zeolites required by the invention therein. This is born out by the FIG. 1. FIG. 1 illustrates that ZSM-5 containing gallium in the framework is more active for toluene disproportionation than ZSM-5 containing non-framework gallium.

Various methods for producing the [Ga] ZSM-5 can be employed.

The catalyst used in the conversion of the invention is a gallium containing crystalline silicate or a gallium containing crystalline alumino silicate, a zeolite, having a characteristic X-ray diffraction pattern. The framework ande nonframework gallium content of these zeolites can be expressed in terms of wt% Ga, and can thus range from 0.1 to 15%. In one embodiment of the invention, the X-ray diffraction pattern of the crystalline silicate containing framework gallium or the crystalline alumino silicate containing framework gallium corresponds to that of ZSM-5. ZSM-5 is disclosed and characterized in U.S. Pat. No. 3,702,886; the X-ray diffraction pattern of ZSM-5 in the U.S. Pat. No. 3,702,886 is incorporated by reference herein. The catalyst used in accordance with the invention may be prepared by modifying the preparation used for preparing ZSM-5 itself. In general, zeolite ZSM-5 can be prepared from a solution containing water, tetrapropyl ammonium hydroxide and the elements of sodium oxide, an oxide of aluminum or gallium, an oxide of silica, and having a composition in terms of mole ratios of oxides, falling within the following ranges:

|  | Broad | Preferred | Particularly Preferred |
|---|---|---|---|
| OH/SiO$_2$ | 0.1–0.8 | 0.1–0.8 | 0.2–0.75 |
| R$_4$N + (R$_4$N + Na+) | 0.2–0.95 | 0.3–0.9 | 0.4–0.9 |
| H$_2$O/OH— | 10–300 | 10–300 | 10–300 |
| YO$_2$/W$_2$O$_3$ | 5–500 | 10–300 | 10–150 | wherein R is propyl, W is aluminum and Y is silicon. This mixture is maintained at reaction conditions until the crystals of the zeolite are formed. Thereafter the crystals are separated from the liquid and recovered. Typical reaction conditions consist of a temperature of from about 75° C. to 175° C. for a period of about six hours to 60 days. A more preferred temperature range is from about 90° to about 150° C., with the amount of at a temperature in such range being from about 12 hours to 20 days. In accordance with the examples below, a typical reaction mixture for the preparation of ZSM-5 was modified to replace the source of aluminum with a source of gallium; although various sources of the gallium may be used, $Ga_2(SO_4)_3$ was used in the examples below. The solid product is separated from the reaction mixture, by cooling the whole to room temperature, filtering and water washing. An alternative method for preparing the gallosilicate is described in our copending application Ser. No. 688,398 filed Jan. 2, 1985. The gallosilicate zeolite can be prepared alternatively by treatment of high silica zeolite with a source of Ga in aqueous solution with a pH greater than 7 at reflux or lowe temperatures; the composite thus treated is ammonium exchanged and calcined to produce a catalyst with increased Bronsted acidity due to the inserted framework elements. The insertion of gallium into a high silica zeolite by this alternative method produces a more crystalline gallosilicate than is possible by crystallization from gels containing hyroxygallium constituents.

The composition of the reaction mixture, set forth in the foregoing table, can be prepared utilizing materials which supply the elements of the appropriate oxide. Such materials include an aluminosilicate, sodium aluminate, alumina, sodium silicate, silica hydrosol, silica gel, silicic acid, sodium hydroxide and tetrapropylammonium hydroxide. Each oxide component of the reaction mixture utilized in preparing the crystalline silicate or the crystalline alumino silicate may be supplied by one or more initial reactants. The reaction mixture can be prepared either batchwise or continuously. Crystal size and crystallization time, will vary with the nature of the reaction mixture employed.

Other methods for forming the framework-gallium ZSM-5 can be employed. In another method, gallium is added to the zeolite starting mixture in the form of salts so that an $SiO_2/Ga_2O_3$ molar ratio of greater than or equal to 100/1 is present in the reaction mixture. In yet another method, gallium is added to the zeolite starting mixture in the form of salts so that an $SiO_2/Ga_2O_3$ molar ratio of less than 100/1 is present in the reaction mixture. Sodium sulfate is added to the reaction mixture when the $SiO_2/Ga_2O_3$ molar ratio is less than 100/1.

In one embodiment, a [Ga]ZSM-5 catalyst is prepared so that a zeolite reaction mixture, from which the catayst is obtained, contains $SiO_2/Ga_2O_3$ ratios of at least 100/1 to 10,000/1. Although $SiO_2/Ga_2O_3$ ratios of greater than 10,000/1 can be used as starting ratios, catalyst containing $SiO_2/Ga_2O_3$ ratios of greater than 10,000/1 reallyhave no practical utility. So the upper limit is defined by the practical utility of such a catalyst. The zeolite reaction mixture may be essentially free of alumina and aluminum. Essentially free of alumina and aluminum, for the purposes of this invention, means that the crystalline product produced will only show the existence of aluminum as an impurity. That is, the silica sol used in the reaction mixture and even the gallium used in the reaction mixture will contain aluminum as an impurity. This impurity will show up in the final product. The zeolite reaction mixture is prepared by mixing, for example, tetrapropylammonium bromide (TPABr) or any other organic template, with sodium hydroxide, a gallium compound, a silica-containing compound or a silica-containing mixture, in water. The zeolite reaction mixture has a composition of hydrogel molar ratios reported in Table I:

TABLE 1

| | |
|---|---|
| $SiO_2/Ga_2O_3 =$ | X |
| $H_2O/SiO_2 =$ | 40 |
| $OH^-/SiO_2 =$ | 0.05 |
| $Na^+/SiO_2 =$ | 0.05 |
| $TPA^+/SiO_2 =$ | 0.10. | wherein X varies from at least 100 to 10,000.

The reaction mixture is heated to a temperture of from 100° to 175° C. for a period of about six hours to sixty days. A preferred temperature range is from about 150° to 175° C. for twelve hours to eight days. The reaction is conducted in an autoclave and is digested with agitation until crystals form. The solid product is separated from the reaction medium by cooling the mixture to room temperature and then washing.

The crystal product is dried at elevated temperatures, for example, at 230° F. for eight to twenty-four hours or it is dried at room temperature under vacuum. The organic template is then burned off in a mixture of nitrogen and oxygen, or pure oxygen, at 1,000° F. for four hours. The catalyst is ion exchanged, for example, with $NH_4NO_3$, and then it is activated by calcination at 1,000° F. in a nitrogen atmosphere.

It is understood that the reaction mixture is not limited to a composition composed of the recited ingredients. Gallium-containing compounds, for example, include gallium sulfate, gallium nitrate, and gallium chloride. The silica source, for example, includes silica hydrosol, silica gel, and silicic acid. The template may be any of the organic templates used to synthesize ZSM-5 catalysts. For example, the template may be tetrapropylammonium hydroxide, tetrapropylammonium bromide or tetrapropylammonium chloride or other organic compounds known to those skilled in the art as successfully-used templates. ZSM-5 catalysts can also be prepared in completely inorganic systems. It is realized that the order of adding or mixing the ingredients is not critical and the reaction mixture can be prepared batchwise or continuously. The critical aspect of this embodiment is that the zeolite reaction mixture contains an $SiO_2/Ga_2O_3$ hydrogel molar ratio of at least 100. The ZSM-5 product obtained from the reaction mixture of the first embodiment is characterized by a framework composed mostly of silicon, oxygen and gallium atoms having an $SiO_2/Ga_2O_3$ ratio of at least 100 and that it contains little or no non-framework gallium. Catalyst containing framework gallium and little or no non-framework gallium can be prepared so that they additionally contain framework aluminum.

In a second embodiment, the ZSM-5 reaction mixture contains the hydrogel molar ratios set forth in Table 1, but X less than 100. To ensure that the product produced contains gallium, where the gallium is primarily present in the framework of the catalyst and the catalyst contains little or no non-framework gallium, sodium sulfate is added to the zeolite reaction mixture. This reaction mixture may be identical to that of embodiment one except for the starting ratio of $SiO_2/Ga_2O_3$ and for the presece of $Na_2SO_4$. The zeolite reaction mixture is heated to about 100° to 175° C. for six hours to sixty days, preferably from about 150° to 175° C. for twelve hours to eight days, with agitation until a crystalline zeolite is formed. The zeolite produced contains gallium, and the gallium is primarily present in the framework of the catalyst. The catalyst additionally contains silicon and oxygen in its framework and has an $SiO_2/Ga_2O_3$ ratio of less than 100, and contains little or no non-framework gallium. The reaction mixture of this second embodiment is not limited to a composition as recited above, but may be composed of other or additional ingredients as is stated in the previously described embodiment.

Typical ion exchange techniques include contacting the ZSM-5 zeolite with a salt of the desired replacing cation or cations. Although a wide variety of salts can be employed, particular preference is given to chlorides, nitrates and sulfates.

Typical replacing cations include hydrogen, ammonium and metal cations, including mixtures of the same. Of the replacing metallic cations, particular preference is made to cations of such metals as manganese and calcium, as well as metals of Group II of the Periodic Table, e.g., zinc, and Group VIII of the Periodic Table, e.g., nickel.

Representative ion exchange techniques are disclosed in a wide variety of patents, including U.S. Pat. Nos. 3,140,249, 3,140,251 and 3,40,253.

Following contact with a salt solution of the desired replacing cation, the zeolites are then preferably washed with water and dried at a temperature ranging from 150° to 600° F. and thereafter calcined for activation in air or inert gases at temperatures ranging from about 500° to 1,500° F. for periods of time ranging from one to forty-eight hours or more.

Regardless of the cations replacing the sodium or other alkali metals, in the synthesized form of the [Ga]ZSM-5 catalyst of the invention, the spatial arrangement of gallium, silicon and oxygen atoms, which form the basic crystal lattic, remains essentially unchanged by the described replacement of sodium and/or alkali metal as determined by taking an X-ray powder diffraction pattern of the ion-exchanged material. Such an X-ray diffraction pattern of an ion-exchanged [Ga]ZSM-5 reveals a pattern substantially the same as that set forth in U.S. Pat. No. 3,702,886, incorporated by reference herein.

The [Ga]ZSM-5 catalysts prepared by the instant invention are formed in a wide variety of particle sizes. Generally speaking, the particles can be in the form of a powder, a granule, or a molded powder, such as an extrudate having a particle size sufficient to pass through a 2-mesh (Tyler) screen and retained on a 400-mesh (Tyler) screen. In cases where the catalyst is molded, such as by extrusion, the product can be extruded before drying or partially dried and then extruded.

As in the case of many other zeolite catalysts, it may be desirable to incorporate in the [Ga]ZSM-5 other materials resistant to temperatures and conditions employed in organic conversion processes. Such materials include active and inactive materials and synthetic or naturally-occurring zeolites, as well as inorganic materials such as clays, silica, and/or metal oxides. The lattermay be either naturally occurring or in the form of gelatinous precipitates including mixtures of silica and metal oxides. The use of an active material in combination with a ZSM-5 can improve the conversion and/or selectivity of the catalysts in certain organic conversion processes. Inactive materials combined with the catalyst serve as diluents to control the amount of conversion in a given process so that products can be obtained economically and in an orderly manner without employing other means for controlling the rate of reaction. Normally, zeolite materials have been incorporated into naturally-occurring clays, for example, bentonite and kaolin, to improve the crush strength of the catalyst under commercial operating conditions.

These materials, i.e., clays, oxides, etc., function as binders for the catalyst. It is desirable to provide a catalyst having good crush strength, because in the environment where these catalyst find use, i.e., in a petroleum refinery, the catalyst is subjected to rough handling which tends to break the catalyst down into powder-like materials causing problems in processing.

Naturally-occurring clays which can be composited with the [Ga]ZSM-5 catalysts of this invention include montmorilloinite and kaolin family members including the sub-bentonites and the kaolins commonly known as Dixie McNamee-Georgia and Florida clays or others in which the main mineral constituent is halloysite, kaolinite, dickite, nacrite, or anauxite. Such clays can be used in their raw state as originally mined or initially subjected to calcination and acid-treated.

In addition to the foregoing materials, the [Ga]ZSM-5 catalysts can be composited with a porous matrix material, such as silica-alumina, silica-magnesia, silica-zirconia, silica-beryllia, silica-titania, as well as ternary compositions such as silica-alumina-zirconia, silica-alumina-thoria, silica-alumina-magnesia, and silica-magnesia-zirconia. The matrix can be in the form of a co-gel.

The catalyst of this invention can be used for the production of high-octane gasoline products. The catalyst shows high activity i.e., selectivity and conversion and improved stability for reactions, such as cracking and light paraffin upgrading, preferably light paraffin upgrading. More particularly, the catalyst can be used for converting $C_2$ to $C_{12}$ paraffins, olefins and naphthenes to high-octane aromatics.

[Ga]ZSM-5 zeolites containing gallium which is primarily present in the framework of the catalyst and which contains little or no non-framework gallium are produced by the methods of Examples 6–12. The zeolite reaction mixtures of these examples contain the following hydrogel ratios:

$$\frac{SiO_2}{Ga_2O_3} = x \quad \frac{H_2O}{SiO_2} = 40 \quad \frac{OH^-}{SiO_2} =$$

$$0.05 \quad \frac{Na^+}{SiO_2} = 0.05 \quad \frac{TPA^-}{SiO_2} = 0.10$$

wherein X is varied in ratios of greater than 100 to 1 according to Examples 6–12 reported in application Ser. No. 141,444, filed Jan. 7, 1988, set forth below.

The invention is illustrated by the following examples. The examples present specific embodiments of the invention, which is to be construed only by the language of the appended claims.

EXAMPLES

EXAMPLE 1

A mixture containing 6.66 g of $Ga_2(SO_4)_3$ in 138 g of $H_2O$ and 31.8 g $H_2SO_4$ was mixed with 36.96 g of TPABr. Na₂SO₄ (29.13 g) in 120 g H₂O with 83.4 silica gel was added to the mixture. The pH of the solution was adjusted to 12 with NaOH solution. Crystallization in an autoclave was at 160° C. for 7 days. The product was filtered, washed, exchanged with NH₄NO₃ and calcined air at 538° C. The composition is designated catalyt No. 3 in Table 2 below.

EXAMPLE 2

The H form of ZSM-5 (SiO$_2$/Al$_2$O$_3$=1,000) was prepared and calcined under N$_2$, exchanged with NH$_4$NO$_3$ and recalcined under air. The composition is designated catalyst No. 1 in Table 2 below.

EXAMPLE 3

The impregnated catalyst was prepared by incipient wetness method with 1 cc solution of 0.6 g Ga(NO$_3$)$_3$ on 3 g HZSM-5 zeolite in Example 2. The catalyst was calcined at 500° C. under air for 2 hours. The composition is designated catalyst No. 2 in Table 2 below.

Ga MAS NMR has been used for quantifying framework Ga (1). Table 2 shows the NMR results and elemental analysis data for the above samples. Example 1 contains predominantly framework Ga with little, if any, non-framework Ga.

EXAMPLE 4

This example illustrates the performance of the above catalysts on toluene disproportionation. Each of the above catalysts was loaded into a reactor and toluene was introduced at 932° F., 600 psig, WHSV=4 and H$_2$/HC mole ratio of 2. Catalyst activity was measured by conversion of toluene.

The composition analysis of the products of Examples 1–3, together with activities of those products are set forth in Table 2.

TABLE 2

| Analytic Data on Ga-containing ZSM-5 | | | |
|---|---|---|---|
| Catalyst | [Al]ZSM-5 | Ga/ZSM-5 | [Ga]ZSM-5 |
| Catalyst | No. 1 | No. 2 | No. 3 |
| Preparation Method | — | impregnation | crystallization |
| wt % Ga, anal. | — | 3.09 | 1.70 |
| wt % Td Ga, NMR | — | ND* | 1.48 |
| wt % Td Ga, TPAD | — | — | 1.66 |
| wt % Al, anal. | 0.11 | 0.101 | 0.017 |
| wt % Td Al, NMR | 0.076 | — | 0.017 |
| alpha | 8 | 182–65 | 32 |
| Toluene % conv. | 11 | 9 | 33 |

*Not detectable

When Alpha Value is examined on aluminosilicate, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the silica alumina cracking catalyst taken as an Alpha of 1 (Rate Constant=0.16 sec$^{-1}$).

The Alpha Test is described in U.S. Pat. No. 3,354,078 and in *The Journal of Catalysis*, Vol. IV. pp. 522–529 (Aug. 1965), each incorporated herein by reference as to that description. The silicate tested in this Alpha Test must be at least partially, in the hydrogen form. The conversion to the hydrogen form may be accomplished by contact of the silicate with an ammonium salt or acid solution followed by thermal treatment to eliminate ammonia and water from the silicate. The following examples serve to illustrate the invention.

When alpha test is performed on metal containing aluminosilicate, the metal dehydrogenation function needs to be considered. The alpha-value of the crystalline silicate containing framework gallium or the crystalline alumino silicate containing framework gallium is not critical per se; it can range from 5 to 300.

The data in FIG. 1 show that Catalyst No. 3 containing zeolitic framework gallium exhibits the highest toluene disproportionation activity (33 weight percent toluene conversion). Compared to catalyst No. 2 which contains much more non-framework gallium than the amount of framework gallium in catalyst No. 3, catalyst No. 3 has much higher toluene disproportionation activity.

EXAMPLE 5

(a) In another preparation, the silicon component was provided as 50 grams Q brand silica in 50 grams of water. The gallium source was provided as a solution of 1.11 grams Ga$_2$(SO$_4$)$_3$, 84.2 grams water and 5.3 grams of H$_2$SO$_4$; 6.16 grams of TPABr (tetrapropylammonium bromide) was used. The Si/Ga$_2$ ratio of the reaction mixture was about 90. The reaction mixture was stirred for several days at 160° C., until product crystallized.

(b) In another procedure for preparing the ZSM-5 containing gallium in its framework, the silica source in the foregoing preparation was replaced by 13.9 grams of extracted silica in 86 grams of water while amounts of other components remained the same as those in the foregoing preparation (a). However, in preparation using extracted silica, stirring of the components for ZSM-5 production was for seven (7) days with addition of 20 cc of 10N NaOH to get a pH of about 10.

(c) In still another preparation, 27.8 g of extracted silica in 86 g of water was used. The gallium source was provided as a solution of 2.22 g Ga$_2$(CO$_4$)$_3$, 84.2 g water and 10.6 g of H$_2$SO$_4$; 12.32 g of TPABr was used. Analysis results of the catalyst compositions of preparations (a), (b) and (c) are set forth below:

TABLE 3

| Catalyst | (a) | (b) | (c) |
|---|---|---|---|
| Elemental Analysis (wt %) | | | |
| SiO$_2$ | 97.7 | 96.0 | 95.1 |
| Al$_2$O$_3$ ppm | 3700 | 86 | 95 |
| Ga | 2.38 | 2.81 | 1.41 |
| Exchange site calc. Meq/g ash | 0.206 | 0.415 | 0.404 |
| TpD meq/g ash | 0.416 | 0.322 | 0.1955 |
| % Ga in framework | 100 | 80 | 95 |
| Alpha | 55 | 60 | 40 |

Each of the products of preparations (a) (b) and (c) of this example exhibited high crystallinity ZSM-5 X-ray diffraction patterns.

(d) In this preparation, the gallosilicate is produced in accordance with our copending application Ser. No. 688,398 filed Jan. 2, 1985. A 6 g sample of HZSM-5 (SiO$_2$/Al$_2$O$_3$=26,000/1) was mixed with 300 cc 0.2N NaOH solution containing 1.5 g of Ga$_2$(SO$_4$)$_3$. The mixture was refluxed for 2 hours and then washed, converted into the ammonium form by exchange with NH$_4$NO$_3$. The resultant zeolite has an exchange capacity of 0.5446 meq/g ash and n-hexane cracking activity of 803.

EXAMPLE 6

In Example 6, which was undertaken by a co-worker, the SiO$_2$/Ga$_2$O$_3$ starting ration used was 100/1. A ZSM-5 catalyst containing framework gallium was prepared by mixing 48.0 grams of silica sol (30.0% silica) with a solution containing 1.03 grams of $Ga_2(SO_4)_3$ and 0.48 grams of NaOH in 139 grams of water. 6.38 grams of tetrapropylammonium bromide was added to the mixture and the pH was checked and adjusted to between pH 12–12.5 by the addition of small amounts of sodium hydroxide. This zeolite reaction mixture was placed in an autoclave and heated at 145°–150° C. and autogenous pressure for two to three days. The product was established as being 100 percent crystalline. Ga-NMR, as explained below, has shown that this product contains gallium which is present primarily in the framework of the catalyst and that the catalyst contains little or no non-framework gallium.

EXAMPLE 7

In another preparation, a mixture containing 27.8 grams of silica gel in 40 grams of water and in the presence of 6.0 grams of NaOH was mixed with 2.2 grams of $Ga_2(SO_4)_3$ wherein the $SiO_2/Ga_2O_3$ hydrogel mole ratio equals 90. 46 grams of $H_2O$ and 10.6 grams of $H_2SO_4$ were added to the reaction mixture along with 12.3 grams of tetrapropylammonium bromide and 9.7 grams of sodium sulfate. The pH of the mixture was adjusted to 10 with sodium hydroxide. The mixture was placed in an autoclave and heated at 160° C. and autogenous pressure for seven days.

Ga-NMR has shown that the product obtained by this method contains gallium which is primarily present in the framework of the catalyst and that the catalyst contains little or no non-framework gallium.

EXAMPLE 8

In Example 8, synthesis of a zeolite product in the presence of gallium was conducted in accordance with Example 7 except sodium sulfate was not added to the reaction mixture. In a typical preparation, a mixture containing 27.8 grams of silica gel in 86 grams of water was mixed with 2.2 grams of $Ga_2(SO_4)_3$ in 84 grams of $H_2O$ (wherein the $SiO_2/Ga_2O_3$ hydrogel molar ratio equals 90). To this mixture was added 10.6 grams of $H_2SO_4$ and 12.3 grams of tetrapropylammonium bromide. The resulting mixture was adjusted to pH 10 with sodium hydroxide solution to prepare a zeolite reaction mixture. The zeolite reaction mixture was placed in an autoclave and heated at 160° C. and autogenous pressure for seven days.

Ga-NMR has shown that this product contains significant amounts of non-framework gallium, i.e., it contains 47% of the total gallium content of the zeolite product.

Nuclear Magnetic Resonance (NMR) is a proven effective tool for identifying, and quantitatively determining, the presence of gallium in the framework of zeolite materials. The identification of the presence of framework gallium in such materials using NMR is called Ga-NMR. The use of Ga-NMR to determine framework gallium is described in the *Journal of Molecular Catalysis*, 1985, 31, 355, the disclosure of which is incorporated by reference herein. The Ga-NMR spectrum has a single broad line with a chemical shift of 155 ppm and the intensity of the Ga-NMR signal, and the value of the chemical shift correspond to the gallium nuclei in the tetrahedral oxygen environment of the zeolite. The conclusion that a [Ga]ZSM-5 product contains gallium primarily present in the framework of the catalyst and which contains little or no non-framework gallium is based on measuring gallium content by Ga-NMR and comparing this measurement with the overall gallium content for a given sample as determined by elemental analysis.

For instance, if the Ga-NMR determination equals that of the elemental gallium analysis for a given sample, it is concluded that the product contains framework gallium. However, if the Ga-NMR determination exceeds that of the elemental gallium analysis for a given sample, it is concluded that the product contains gallium primarily present in the framework of the catalyst and that the catalyst contains little or no non-framework gallium. If the Ga-NMR determination is less than the gallium elemental analysis, the product contains both framework and a significant amount of non-framework gallium. The amount of non-framework gallium in this third method is determined by subtracting the Ga-NMR determination from the Ga elemental analysis result.

Table 4 sets forth the results showing that the [Ga]ZSM-5 catalyst synthesized in Example 6 show that the zeolite produced contains gallium which is primarily present in the framework and that the catalysts contain little or no non-framework gallium. This result is contrasted with the result obtained by the method of Example 8. The catalyst produced by the method of Example 8 contains both framework and significant amounts of non-framework gallium.

TABLE 4

Ga—MASNMR and Analytical Data for Determining Presence of Framework Gallium in [Ga]ZSM-5 Samples

| | Starting Grams $Ga_2(SO_4)_3$ | Starting Molar Ratio $SiO_2/Ga_2O_3$ | % Ga. NMR | % Ga. Anal. | % Non-Framework Ga | % $Al_2O_3$. Anal. |
|---|---|---|---|---|---|---|
| Ex. 6 | 1.03 | 100/1 | 2.3 | 2.04 | 0 | 0.058 |
| Ex. 7 | 2.2 | 90/1 | 1.6/1.0* Avg. = 1.3 | 1.16 | Avg. = 0 | 0.037 |
| | | Previous two conditions for $SiO_2/Ga_2O_3$ not met. | | | | |
| Ex. 8 | 2.2 | 90/1 | 0.81 | 1.54 | .47 | 0.010 |

*Two NMR determinations.

What is claimed is:

1. A catalytic process for toluene disproportionation comprising
   contacting a toluene containing feedstock with a catalyst comprising a crystalline silicate exhibiting the X-ray diffraction pattern of ZSM-5 wherein said crystalline silicate comprises 0.1 to 5 weight percent gallium, wherein said gallium is a framework element in said crystalline silicate, said contacting being undertaken under conditions effective to convert toluene to toluene disproportionation products; and
   converting said toluene to said products in a conversion which exceeds that effected by ZSM-5 containing non-framework gallium under identical conditions.

2. The process of claim 1, wherein said conditions include a temperature ranging from 750° to 1100° F. and a pressure of 100 to 800 psig.

3. The process of claim 2, wherein said temperature ranges from 850° to 950° F.

4. The process of claim 1, wherein said crystalline silicate is made by cocrystallization.

5. The process of claim 1, wherein said contacting is undertaken in the presence of hydrogen.

* * * * *